(12) United States Patent
Harkema et al.

(10) Patent No.: US 10,688,302 B2
(45) Date of Patent: Jun. 23, 2020

(54) METHODS FOR APPLYING EPIDURAL ELECTRICAL STIMULATION

(71) Applicant: UNIVERSITY OF LOUISVILLE RESEARCH FOUNDATION, INC., Louisville, KY (US)

(72) Inventors: Susan J. Harkema, Louisville, KY (US); Yangshen Chen, Louisville, KY (US); Manikandan Ravi, Louisville, KY (US); Claudia Angeli, Louisville, KY (US); Charles Hubscher, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 139 days.

(21) Appl. No.: 15/752,307

(22) PCT Filed: Aug. 18, 2016

(86) PCT No.: PCT/US2016/047547
§ 371 (c)(1),
(2) Date: Feb. 13, 2018

(87) PCT Pub. No.: WO2017/031314
PCT Pub. Date: Feb. 23, 2017

(65) Prior Publication Data
US 2018/0229036 A1  Aug. 16, 2018

Related U.S. Application Data

(60) Provisional application No. 62/206,621, filed on Aug. 18, 2015.

(51) Int. Cl.
*A61N 1/00* (2006.01)
*A61N 1/36* (2006.01)
(Continued)

(52) U.S. Cl.
CPC ....... *A61N 1/36062* (2017.08); *A61N 1/0551* (2013.01); *A61N 1/0553* (2013.01);
(Continued)

(58) Field of Classification Search
CPC .............. A61N 1/36062; A61N 1/0551; A61N 1/36125; A61N 1/37211; A61N 1/0553;
(Continued)

(56) References Cited

U.S. PATENT DOCUMENTS

| 6,516,227 | B1 | 2/2003 | Meadows et al. |
| 2006/0161235 | A1* | 7/2006 | King .................... A61N 1/0553 607/117 |

(Continued)

FOREIGN PATENT DOCUMENTS

| RU | 52715 | 4/2006 |
| WO | 2008/070145 | 6/2008 |

(Continued)

OTHER PUBLICATIONS

International Search Report and Written Opinion of the International Searching Authority for PCT/US2016/047547, dated Oct. 27, 2016.

(Continued)

*Primary Examiner* — Mallika D Fairchild
(74) *Attorney, Agent, or Firm* — Dentons Bingham Greenbaum LLP; Brian W. Chellgren

(57) ABSTRACT

Embodiments of the present invention relate to methods for applying epidural electrical stimulation to improve motor function or physiological responses in paralyzed individuals. More particularly, the present invention relates to methods for creating and applying specific configurations of epidural stimulation to assist or cause a patient to perform a complex motor function or to mitigate one or more secondary consequences of paralysis including, but not limited to, cardio- (Continued)

vascular, respiratory, bladder, temperature and sexual dysfunction.

8 Claims, 6 Drawing Sheets

(51) Int. Cl.
*A61N 1/05* (2006.01)
*A61N 1/372* (2006.01)

(52) U.S. Cl.
CPC ..... *A61N 1/36003* (2013.01); *A61N 1/36125* (2013.01); *A61N 1/37211* (2013.01); *A61N 1/36007* (2013.01); *A61N 1/3611* (2013.01); *A61N 1/36103* (2013.01); *A61N 1/36107* (2013.01); *A61N 1/36114* (2013.01); *A61N 1/36185* (2013.01)

(58) Field of Classification Search
CPC ............ A61N 1/36003; A61N 1/36107; A61N 1/36007; A61N 1/36103; A61N 1/3611; A61N 1/36114; A61N 1/36185
See application file for complete search history.

(56) References Cited

U.S. PATENT DOCUMENTS

2014/0172045 A1* 6/2014 Yip .................... A61N 1/36185
607/59
2014/0180361 A1 6/2014 Burdick et al.

FOREIGN PATENT DOCUMENTS

WO 2014/093178 6/2014
WO 2014093178 A2 6/2014

OTHER PUBLICATIONS

Extended European Search Report, International application No. PCT/US16/047547, Applicant University of Louisville Research Foundation, Inc., dated Feb. 22, 2019.

* cited by examiner

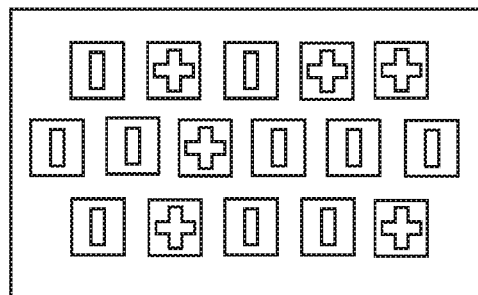
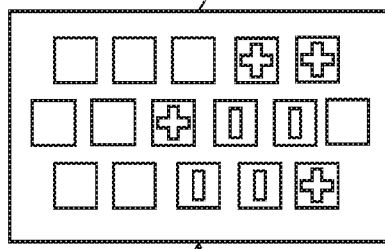
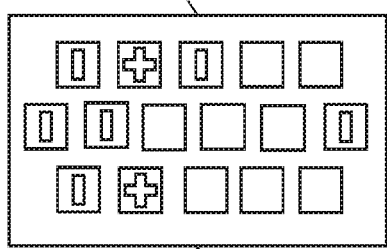
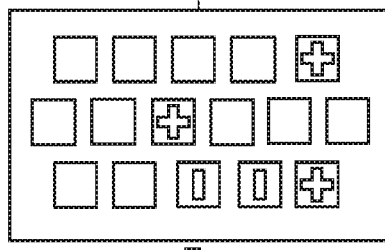
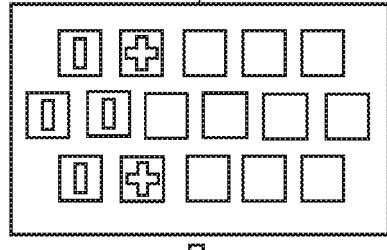
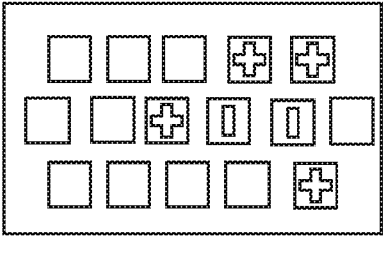
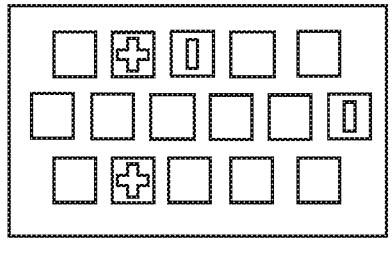
FIG. 2

METHODS FOR APPLYING EPIDURAL ELECTRICAL STIMULATION

This application claims the benefit of U.S. provisional patent application Ser. No. 62/206,621, filed 18 Aug. 2015, for METHODS FOR DETERMINING CONFIGURATIONS OF EPIDURAL STIMULATION FOR MOTOR FUNCTION AND OTHER PHYSIOLOGICAL RESPONSES, incorporated herein by reference.

This invention was made with government support under grant no. R01HD080205 awarded by the National Institutes of Health. The United States government has certain rights in the invention.

FIELD OF THE INVENTION

Embodiments of the present invention relate to methods for applying epidural electrical stimulation to improve motor function or physiological responses in paralyzed individuals. More particularly, the present invention relates to methods for creating and applying specific configurations of epidural stimulation to assist or cause a patient to perform a complex motor function or to mitigate one or more secondary consequences of paralysis including, but not limited to, cardiovascular, respiratory, bladder, temperature and sexual dysfunction.

BACKGROUND

Serious spinal cord injuries (SCI) result in partial (incomplete) or substantially complete loss of sensory motor function below the level of the spinal lesion. For individuals with complete or incomplete loss of motor function, substantial recovery of standing and stepping recovery has been demonstrated with task specific physical rehabilitation training. Recently, task specific physical rehabilitation training has been combined with epidural stimulation (ES) of the spinal cord in patients with incomplete and complete motor paralysis. High density epidural stimulating electrode arrays can provide spatially selective stimulation to regions of the spinal cord to facilitate or cause muscle movement. Mapping the spinal cord of patients for delivery of electrical stimulation has been performed for other applications, such as pain management, but has not been performed for the purpose of aiding patients with SCI in performing complex motor movements. Generating functional standing, stepping and other motor movements in patients with SCI requires the assembly and delivery of sophisticated stimulation patterns which are task-specific and patient-specific, and require a smooth transition between distinct ES programs, each of which remain a challenge. In addition, secondary consequences of paralysis can also be mitigated by sophisticated ES patterns specific to the physiological response and to the individual. In contrast, typical commercially available spinal cord stimulating systems used for pain management and other applications are designed to run only one ES program at a time, either in a single iteration or in a repeated loop.

SUMMARY

In the context of studies of human locomotion, we made the unexpected observation that individuals who had been diagnosed as having clinically motor complete spinal cord injuries, that is, being unable to voluntarily activate muscles below their level of lesion, developed the ability to voluntarily move their toes, ankles, knees and hips only in the presence of tonic ES of the lumbosacral spinal cord when also receiving intense locomotor training. Even more unexpected, over a period of months, the patients reported mitigation of secondary consequences of paralysis, including improved temperature regulation, bowel and bladder function, and normalized sexual activity. We also measured significant improvements in cardiovascular and respiratory function that persisted throughout the day even without stimulation. Our research indicates that ES aids in the recovery of significant levels of autonomic control of cardiovascular and respiratory function as well as the ability to voluntarily control leg movements below the injury level. ES intervention would provide an immediate therapeutic alternative to individuals who currently have no recourse for treatment. Such intervention would result in significant reductions of cost to the health care system, caregivers and society.

It will be appreciated that the various apparatus and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

FIG. 2 is a diagram of electrode arrays depicting assembly of an electrostimulation sequence from two cohorts, each cohort including two basic units of electrodes.

DETAILED DESCRIPTION OF THE PREFERRED EMBODIMENTS

Figure 1A:
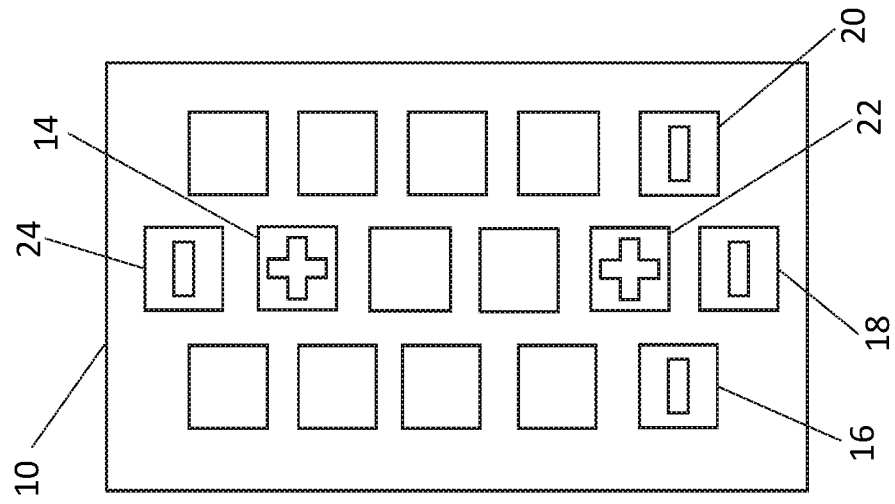
FIGS. 1A, 1B and 1C are diagrams of electrode arrays depicting exemplary basic units of electrodes.

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document herein is a reference to an embodiment of a family of inventions, with no single embodiment including features that are necessarily included in all embodiments, unless otherwise stated. Further, although there may be references to "advantages" provided by some embodiments of the present invention, it is understood that other embodiments may not include those same advantages, or may include different advantages. Any advantages described herein are not to be construed as limiting to any of the claims.

Specific quantities (spatial dimensions, angles, dimensionless parameters, etc.) may be used explicitly or implicitly herein, such specific quantities are presented as examples and are approximate values unless otherwise indicated. Discussions pertaining to specific compositions of matter are presented as examples and do not limit the applicability of other compositions of matter, especially other compositions of matter with similar properties, unless otherwise indicated.

The specific combination of epidural stimulation with precise and optimized stimulation configurations and intense task specific training has led to recovery of function and physiological responses not previously seen in individuals with severe paralysis. The optimization of configurations for each task, motor behavior or physiological response is the novel strategy of generating unique and specific electrical fields in the use of epidural stimulation to recover motor function and physiological responses including, but not limited to, standing, stepping, voluntary autonomic function, cardiovascular function, bowel function, bladder function, temperature regulation, blood flow and circulation, respiratory function, metabolic function and cognition in paralyzed individuals.

The present invention requires detailed mapping of motor-evoked responses relative to electrode stimulation site, frequency, pulse width and stimulation intensity. The process of mapping the responses at low frequency with stimulations at different locations in the electrode array provides a blueprint of the spinal cord excitability patterns that guide the selection of more complex configurations used for motor behavior, physiological responses and task specific training. Maps of activation for each muscle are developed to identify areas of the electrode, frequency, pulse width and stimulation intensities where agonist and antagonist activity are present for motor behavior. Maps of activation for physiological responses are developed to identify areas of the electrode, frequency, pulse width and stimulation intensities where the biologically appropriate responses are optimized. The combination of the defined stimulation configurations with task specific motor training regimens and specific training of cardiovascular, respiratory, bladder and bowel activity elicits the optimal behavior and physiological responses.

Figure 1B:
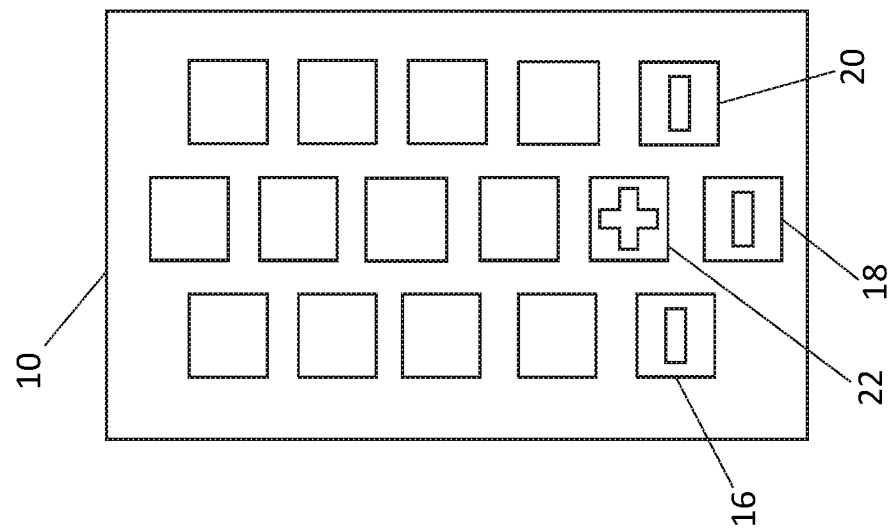
Figure 1C:
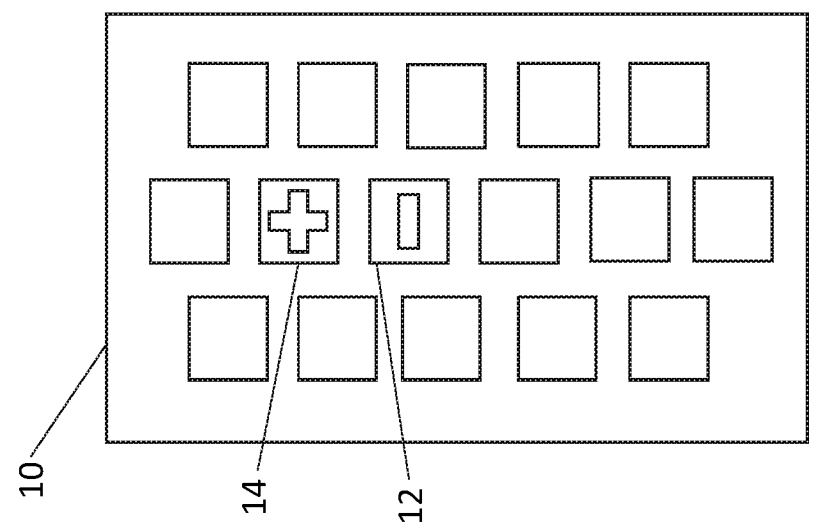

Referring to FIGS. 1A-C, an exemplary electrode array 10 comprising a plurality of electrodes disposed on a flexible biocompatible material is provided. In other embodiments, other high density electrode arrays may be used. Preferably, the electrodes comprise one or more biocompatible metals or alloys, as known in the art. In the embodiments depicted in FIGS. 1A-C, the electrode array 10 includes fifteen electrodes. In further embodiments, additional or fewer electrodes may be provided. Each electrode on the pad may be configured to function as an anode, a cathode, or high impedance to inhibit current flow. Electrodes functioning as stimulation electrodes, which may be cathodes or anodes, deliver electric pulses with defined frequency, amplitude, pulse width, and onset and end times.

In various embodiments, the electrode array 10 is operably linked to control circuitry that permits selection of electrodes for activation, also referred to as stimulation, and that controls the electrode configuration, i.e., whether the electrode functions as an anode, cathode or high impedance; and the frequency, amplitude, pulse width, and onset and end times of the electric pulse delivered through the electrodes. In certain embodiments, each variable is independently selectable and controllable for each individual electrode. In some embodiments, the electrode array is operatively connected to a pulse generator, such as a battery or other source of electric current. In certain embodiments, the electrode array, pulse generator and control circuitry are implanted in a patient. In certain embodiments, the control circuitry includes a controller, such as a microprocessor, computer readable storage media, such as recordable computer memory, a receiver for receiving electronic data, including but not limited to electrostimulation programs and protocols, and an amplitude driver for scaling voltages of pulses delivered from the pulse generator to the electrode array.

A group of electrodes consisting of at least two electrodes, and comprising at least one anode and at least one cathode, and each having substantially identical frequencies, pulse width, amplitude, and onset and end times, is referred to herein as a basic unit or primary subgroup. Different basic units may share common electrodes as ground.

FIGS. 1A-C depict basic units including two, four, and six electrodes. FIG. 1A depicts an electrode array 10 including a basic unit including two electrodes. The exemplary basic unit shown in FIG. 1A is a cathode-driven stimulation system, where cathode 12 is the stimulation electrode generating an electrical pulse with a frequency of 35 Hz, a pulse width of 200 µs and an amplitude of 4V. Anode 14 is the ground. Electrodes displayed without minus (−) or plus (+) signs function as high impedance and do not play an active role in this basic unit. FIG. 1B depicts the electrode array 10 with a different pattern of activated electrodes, displaying a basic unit including four electrodes. The exemplary basic unit shown in FIG. 1B is a cathode-driven stimulation system, where cathode 16 is a stimulation electrode generating an electrical pulse with a frequency of 70 Hz, a pulse width of 400 µs, and an amplitude of 10V, cathode 18 is a stimulation electrode generating an electrical pulse with a frequency of 70 Hz, a pulse width of 400 µs and an amplitude of 6.5V, and cathode 20 is a stimulation electrode generating an electrical pulse with a frequency of 70 Hz, a pulse width of 400 µs and an amplitude of 3V. Anode 20 the ground. FIG. 1C depicts the electrode array 10 with a further pattern of activated electrodes, displaying a basic unit including six electrodes. The exemplary basic unit shown in FIG. 1C is a cathode-driven stimulation system, where cathodes 16, 18 and 20 are stimulation electrodes generating electrical pulses as described in connection with FIG. 1B, and cathode 24 is a stimulation electrode generating an electrical pulse with a frequency of 70 Hz, a pulse width of 400 µs and an amplitude of 4V. Anodes 14 and 22 are ground. In other embodiments, other electrodes or combinations of electrodes in the electrode array 10 may be activated to create other basic units. In further embodiments, a basic unit may be an anode-driven stimulation system wherein the anode(s) is the stimulation electrode and the cathode(s) is the ground.

Referring now to FIG. 2, a cohort or secondary subgroup is a group of electrodes consisting of at least one basic unit. In some embodiments, basic units are grouped into cohorts such that stimulation of a cohort generates a predetermined physiological or motor response, such as flexing the patient's calf muscle. In certain embodiments, a cohort includes at least one basic unit and, in further embodiments, includes at least two and not more than fifteen basic units. In other embodiments, electrodes are grouped into cohorts without previously grouping the electrodes into basic units. All stimulation electrodes within a cohort have the same frequency, pulse width, and onset/end time, but their amplitudes may differ. FIG. 2 depicts an exemplary first cohort 21, including eight electrodes from basic units 22, 23. FIG. 2 also depicts an exemplary second cohort 24, including eight electrodes from basic units 25, 26. As indicated in FIG. 2, a cohort may include basic units which share ground electrodes (cathodes, in this example) in common such that multiple stimulation electrodes (anodes, in this example) share ground electrodes.

A sequence or tertiary subgroup is a group of electrodes consisting of at least one cohort, wherein each electrode in the sequence shares the same onset time and end time. Cohorts are grouped into sequences such that stimulation of a sequence generates a more complex physiological or motor response. For example, a sequence designed to promote a walking motion in patient's right leg, may include a cohort stimulating the patient's calf muscle, a cohort stimulating the patient's quadriceps muscles, and a cohort stimulating the patient's hamstring muscles. Individual electrodes within a sequence are not assigned to multiple cohorts within the sequence, such that there are no electrodes shared between cohorts within a given sequence. Different cohorts in a sequence may have different frequencies and pulse widths, but have the same onset and end times. FIG. 2 depicts a sequence 28 consisting of the first cohort 21 and second cohort 24.

A program is a collection of one or more sequences activated in defined timing order to perform a specific motor behavior or physiological response (e.g. standing, walking, voiding bladder, maintain blood pressure etc.). Each sequence defines its timing information such as delay, cycle on duration, and cycle off duration inside a program. For example, a program designed to promote walking may include two sequences, one promoting a walking motion in the patients right leg and another promoting a walking motion in the patient's left leg.

Figure 3:
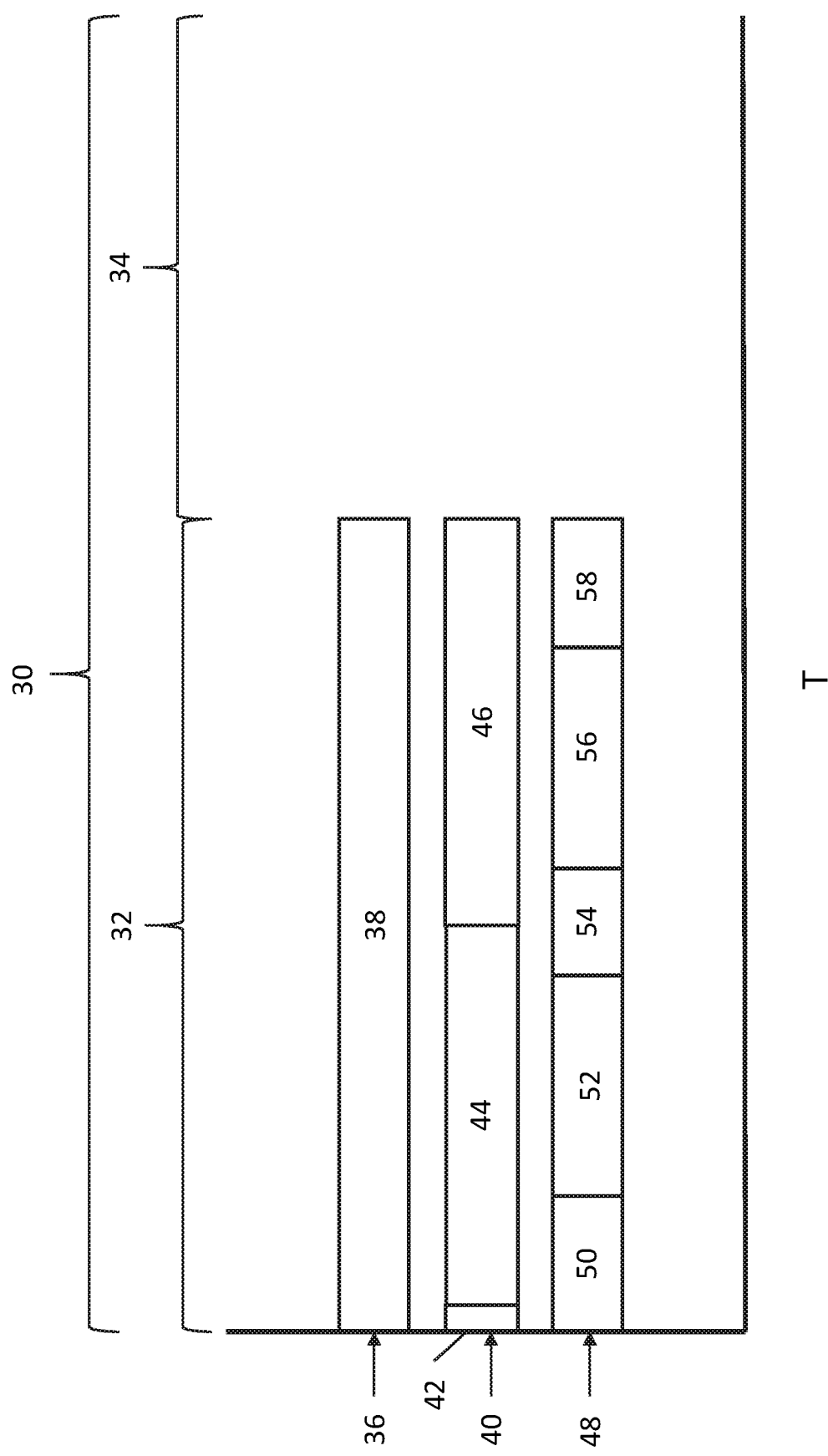
FIG. 3 is a diagram depicting an electrostimulation program consisting of four sequences with specific timing information for each sequence.

FIG. 3 schematically depicts a program 30 consisting of three sequences, each sequence represented by a horizontal row, the horizontal length of each element representing the relative duration of that element in time (T). The program 30 includes an on cycle 32 during which one or more sequences in the program may actively provide ES, followed by an off cycle 34 during which no sequence provides ES. In the depicted program 30, the on cycle 32 has a duration of thirty seconds and the subsequent off cycle 34 has a duration of twenty seconds. Each sequence within the program 30 is configured to include at least one on cycle of a predetermined duration, optionally, a delay between the initiation of the program on cycle and the initiation of the sequence on cycle, optionally, at least one off cycle of a predetermined duration, and optionally may be configured to repeat the sequence on cycle at the end of the sequence off cycle. In the depicted program 30, the first sequence 36 does not include a delay and includes an on cycle period 38 of thirty seconds, such that the first sequence 36 actively provides stimulation during the entirety of the thirty second duration program on cycle 32. The second sequence 40 includes a delay 42 of one second, followed by an on cycle period 44 of fourteen seconds, followed by an off cycle period 46 of fifteen seconds, whereby the delay 42, on cycle period 44, and off cycle period 46 collectively last for the entirety of the thirty second program on cycle 32. The third sequence 48 includes a delay 50 of five seconds, followed by an on cycle period 52 of eight seconds, followed by an off cycle period 54 of four seconds. The third sequence 48 is configured to repeat, therefore, the off cycle period 54 is followed by a second on cycle period 56 of eight seconds, followed by a second off cycle period 58 lasting until the end of the program on cycle 32.

As should be understood, the number of sequences in a given program, the presence or absence of delays in a given sequence, the length of program and sequence on cycles and off cycles, and other elements in the configuration of a program will vary based on the individual patient and based on the motor activity or physiological response generated by the program. Furthermore, electrodes within a given sequence are not actively delivering electrical charge to the patient during the entirety of the sequence's on cycle. Instead, pulses are delivered in intervals as dictated by the pulse frequency. It is possible in programs including multiple sequences operating in parallel, such as the exemplary program shown in FIG. 3, that two sequences may attempt to deliver pulses at identical times using the same electrodes. Such event is referred to a pulse overlap or collision. In the event of an imminent collision, a slight delay (typically in the single digits of milliseconds) is added to one of the sequences to avoid such collision.

Figure 4:
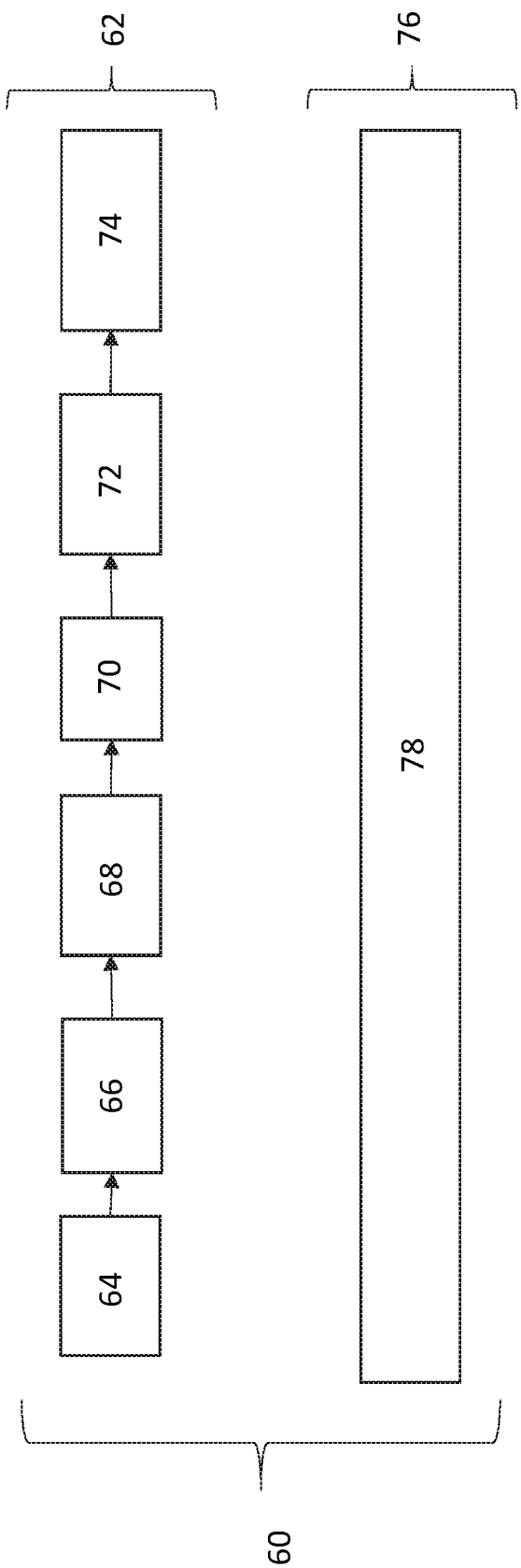
FIG. 4 is a flowchart depicting an electrostimulation protocol including two lines enacted in parallel, each line including two electrostimulation programs enacted in series.

Referring now to FIG. 4, a protocol is a group of programs activated in series or parallel to perform a complex motor function, such as a patient approaching a toilet, sitting down on the toilet, then voiding his or her bowels. Each individual program targets a single motor function, such as standing or voiding. A protocol enacts more complicated tasks which requires coordination of a series of motor functions. One example protocol is "To Void", which assists the patient in standing up, walking to a toilet, sitting on down on the toilet, and voiding his or her bowels. In some embodiments, a protocol performing complex motor control activities, such as the exemplary "To Void" program, also includes one or more programs performing physiological functions apart from complex motor control activities. For example, the "To Void" protocol may include the "Sitting Position to Standing Position" program, the "Walking" program, the "Standing Position to Sitting Position" program, and the "Voiding Bowels" program activated in series, while a program providing ES to maintain the patient's blood pressure within a safe range is simultaneously activated in parallel. The running-time of each program and inter-program delay are configured in a protocol. Programs in a protocol can run in series, in parallel, or in combinations of the two.

FIG. 4 displays a single protocol 60 including two series of programs or "lines" run in parallel. The first line 62 includes first program 64, the "Sitting Position to Standing Position Program", which is active for a predetermined duration, followed by a predetermined delay 66, followed by second program 68, the "Walking" program, which is active for a predetermined duration, followed by a predetermined delay 70, followed by the third program 72, the "Standing Position to Sitting Position" program, followed immediately by the fourth program 74, the "Voiding Bowels" program. The second line 76 runs in parallel to the first line 62 and includes a single program 78, which remains active for the duration of the entire series of programs and delays in the first line 62. In some embodiments, the single program 78 is a program designed to maintain the patient's blood pressure within a safe range.

In some embodiments, a line or lines may be followed by a decision point, after which the line may reach an end or may undergo a reset and start from the beginning by running the initial program in the line again. For example, the first line 62 described above would typically be run a single time then ended, as it is rarely necessary to void one's bowels in rapid succession. Alternatively, the second line 76 described above may be run on a repeated cycle throughout the day to maintain the patient's blood pressure. While the exemplary protocol depicted in FIG. 4 includes a series of programs running in parallel with a single program, it should be understood that other protocols may include additional or fewer programs, and such programs may be run in series, in parallel, or in a combination of the two, as needed to perform complex motor control activities and physiological activities in the individual patient.

Figure 5:
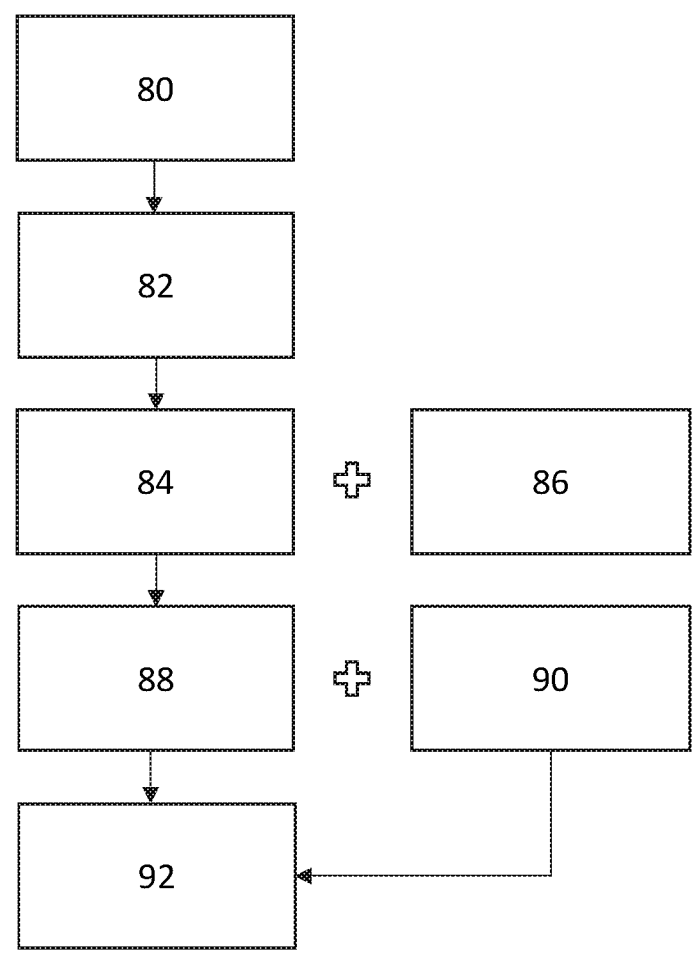
FIG. 5 is a flowchart depicting a process for providing electrostimulation to a patient to facilitate a patient performing a complex task.

By initiating the complex pattern of electrode stimulation described by a protocol in an implanted electrode array, specific regions of the spine are stimulated to perform a complex motor function, temperature regulation, cardiovascular, respiratory, bowel, bladder and/or sexual function. Such stimulation is combined with intense locomotor training. An exemplary process for facilitating performance of a complex motor function is depicted in FIG. 5. In initial step 80, a neurostimulator is implanted in a patient with SCI. The neurostimulator includes an electrode array positioned within the patient to apply stimulation to the lumbosacral spinal cord. In subsequent step 82, the patient's spinal cord is mapped by activating electrodes and combinations of electrodes in the electrode array to determine the results of each stimulation pattern. For example, experimental testing may determine that activation of a group of three electrodes causes the patient's right calf muscle to flex, and these electrodes may be designated as a cohort. In subsequent step 84, combinations of electrodes and specific timing of electrode activations are identified for performing individual tasks, such as standing up, walking, or sitting down, are identified and designated as programs. For example, creating a walking motion involves stimulating various leg muscles with a specific timing pattern which may vary based on the length of the patient's leg, the strength of the various muscles, the desired walking speed, and other factors. Preferably, identification of combinations of electrodes to perform a task in step 84 is combined with task specific training 86 for the patient to perform the same task. For example, stimulation promoting walking may be applied to the patient while a physical therapist assists the patient in walking. The timing of various cohorts, sequences, programs and protocols may be modified based on the patient's results. Proceeding to step 88, for complex tasks requiring multiple individual tasks, such as, for example, a patient standing up, walking, sitting down, then voiding his or her bowels, the timing of each individual program for performing such individual task is determined and specified for the specific patient. The programs necessary to perform the complex task and their respective timing are designated a protocol. Preferably, determining and specifying timing in step 88 is combined with complex task specific training 90 for the patient to perform the same complex task, such as building the patient's strength, stamina and coordination for performing the complex task by practicing the individual tasks separately and in combination. In final step 92, the patient receives electrostimulation according to the protocol and utilizes the task specific training to perform the complex task without assistance from technicians or physical therapists.

Figure 6A:
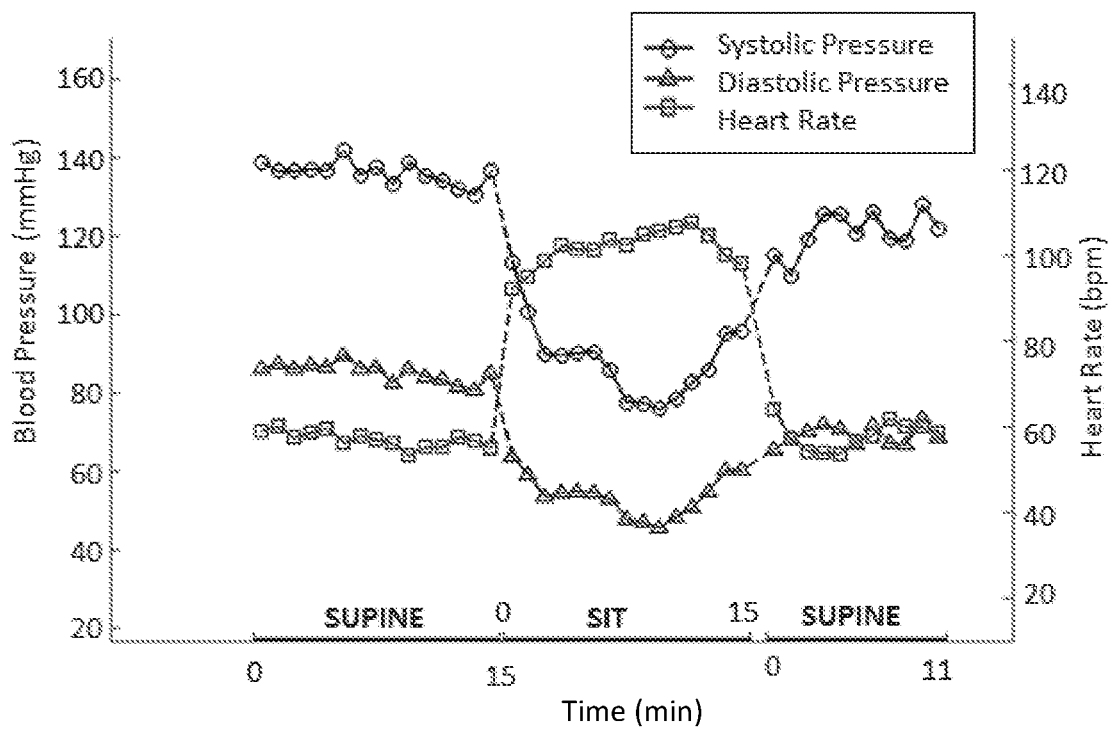
FIG. 6A is a graph depicting the systolic and diastolic blood pressure and heart rate of a patient as the patient transitions between supine and sitting positions.
Figure 6B:
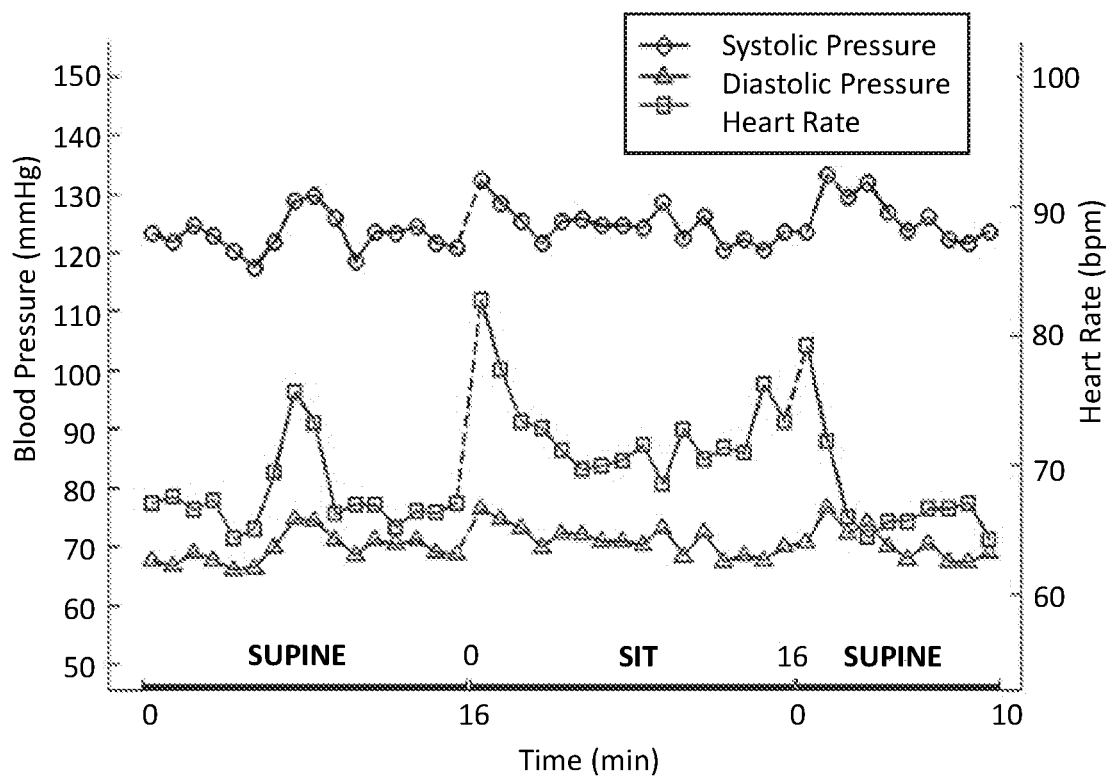
FIG. 6B is a graph depicting systolic and diastolic blood pressure and heart rate of the patient in FIG. 6A as the patient transitions between supine and sitting positions after receiving electrostimulation and training.

FIGS. 6A and 6B shows the effectiveness of the training and electrostimulation process described above. FIG. 6A depicts the systolic and diastolic blood pressure and the heart rate of a patient transitioning from a supine position to a sitting position and back to a supine position. FIG. 6B depicts the same characteristics of the same patient after eighty sessions of training in combination with epidural stimulation, including stimulation to regulate blood pressure and heart rate while transitioning between positions. As is clearly visible, the dramatic decrease in blood pressure in the sitting position has been substantially eliminated and the increase in heart rate has been substantially reduced.

Various aspects of different embodiments of the present invention are expressed in paragraphs X1, X2, and X3 as follows:

X1. One aspect of the present invention pertains to a method for electrical epidural stimulation to a patient, including providing an implantable electrode array comprising a plurality of electrodes, wherein at least one of the plurality of electrodes is configured to deliver one or more electric pulses, wherein each pulse includes a frequency, a pulse width, an amplitude, an onset time, and an end time; grouping electrodes configured to deliver electric pulses with identical onset times and identical end times into at least one sequence; grouping at least one sequence into a program, the program configured to deliver electrical epidural stimulation causing the patient to perform a specific motor function or physiological response; and delivering electrical stimulation to the patient, via the electrodes, according to the program.

X2. Another aspect of the present invention pertains to a neurostimulator-implemented method, including providing an implantable neurostimulator comprising a pulse generator operatively connected to an electrode array configured to deliver electrical stimulation to a patient's spinal cord, the electrode array including a plurality of electrodes; storing programs of electrode activation, each program configured to deliver electrical stimulation causing the patient to perform a specific motor function or physiological response; storing at least one protocol of electrode activation, each protocol including at least one program; and delivering electrical stimulation specified in the at least one protocol.

X3. A further aspect of the present invention pertains to a neurostimulator-implemented method, including providing an implantable neurostimulator comprising a pulse generator operatively connected to a plurality of electrodes configured to deliver electrical stimulation to a human patient; defining a protocol of electrical stimulation, the protocol causing the patient to perform non-identical first and second motor functions; and delivering to the patient, via the electrodes, electrical stimulation according to the protocol.

Yet other embodiments pertain to any of the previous statements X1, X2, or X3 which are combined with one or more of the following other aspects.

Further including grouping electrodes configured to deliver electric pulses with identical onset times, identical end times, identical frequencies, and identical pulse widths into at least one cohort, and wherein said grouping electrodes configured to deliver electric pulses with identical onset times and identical end times into at least one sequence comprises grouping at least one cohort into at least one sequence.

Further including grouping electrodes configured to deliver electric pulses with identical onset times, identical end times, identical frequencies, identical pulse widths, and identical amplitudes into basic units, and wherein grouping electrodes configured to deliver electric pulses with identical onset times, identical end times, identical frequencies, and identical pulse widths into at least one cohort comprises grouping at least one basic unit into at least one cohort.

Wherein the frequency, pulse width, amplitude, onset time and end time of each electrode in the plurality of electrodes is independently controllable.

Wherein the program includes an on cycle period and an off cycle period.

Wherein, during the on cycle period, at least one sequence in the program delivers electrical epidural stimulation to the patient, and wherein, during the off cycle period, no sequence in the program delivers electrical epidural stimulation to the patient.

Wherein grouping at least one sequence into the program includes grouping a plurality of sequences into the program.

Further including grouping at least one program into a protocol.

Wherein grouping at least one program into a protocol includes grouping a plurality of programs into a protocol, the protocol being configured to deliver electrical epidural stimulation causing the patient to perform a plurality of specific motor functions or physiological responses.

Further including providing a patient user interface in communication with the implantable neurostimulator.

Wherein said delivering occurs upon the neurostimulator receiving an activation signal from the patient user interface.

Wherein the patient user interface is a portable computing device.

Wherein said storing occurs in a recordable memory operatively connected to the pulse generator.

Wherein the at least one protocol includes a plurality of programs.

Wherein the plurality of programs includes at least two programs configured to activate in series.

Wherein the plurality of programs includes at least two programs configured to activate in parallel.

Wherein one of the programs is configured to deliver electrical stimulation causing the patient to perform the specific motor function and wherein another of the programs is configured to deliver electrical stimulation causing the patient to perform a physiological response.

Wherein the electrical stimulation is epidural stimulation.

Wherein the protocol includes a delay between delivery of electrical stimulation causing the patient to perform the first motor function and delivery of electrical stimulation causing the patient to perform the second motor function.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method for electrical epidural stimulation to a patient, comprising:

providing an implantable electrode array comprising a plurality of electrodes, wherein at least one of the plurality of electrodes is configured to deliver one or more electric pulses, wherein each pulse includes a frequency, a pulse width, an amplitude, an onset time, and an end time;

grouping electrodes configured to deliver electric pulses with identical onset times, identical end times, identical frequencies, and identical pulse widths into at least one cohort;

grouping at least one cohort configured to deliver electric pulses with identical onset times and identical end times into at least one sequence, wherein each electrode is not grouped into more than one cohort within each sequence;

grouping at least one sequence into a program, the program configured to deliver electrical epidural stimulation causing the patient to perform a specific motor function or physiological response; and delivering electrical stimulation to the patient, via the electrodes, according to the program.

2. The method of claim 1, further comprising grouping electrodes configured to deliver electric pulses with identical onset times, identical end times, identical frequencies, identical pulse widths, and identical amplitudes into basic units, and wherein grouping electrodes configured to deliver electric pulses with identical onset times, identical end times, identical frequencies, and identical pulse widths into at least one cohort comprises grouping at least one basic unit into at least one cohort.

3. The method of claim 1, wherein the frequency, pulse width, amplitude, onset time and end time of each electrode in the plurality of electrodes is independently controllable.

4. The method of claim 1, wherein the program includes an on cycle period and an off cycle period.

5. The method of claim 4, wherein, during the on cycle period, at least one sequence in the program delivers electrical epidural stimulation to the patient, and wherein, during the off cycle period, no sequence in the program delivers electrical epidural stimulation to the patient.

6. The method of claim 1, wherein grouping at least one sequence into the program includes grouping a plurality of sequences into the program.

7. The method of claim 1, further comprising grouping at least one program into a protocol.

8. The method of claim 1, wherein grouping at least one program into a protocol includes grouping a plurality of programs into a protocol, the protocol being configured to deliver electrical epidural stimulation causing the patient to perform a plurality of specific motor functions or physiological responses.

* * * * *

UNITED STATES PATENT AND TRADEMARK OFFICE
CERTIFICATE OF CORRECTION

PATENT NO. : 10,688,302 B2
APPLICATION NO. : 15/752307
DATED : June 23, 2020
INVENTOR(S) : Susan J. Harkema et al.

Page 1 of 1

It is certified that error appears in the above-identified patent and that said Letters Patent is hereby corrected as shown below:

On the Title Page

Item (72) please correct the first name of the inventor from "Yangshen" to --Yangsheng--.

Signed and Sealed this
Eleventh Day of October, 2022

Katherine Kelly Vidal
*Director of the United States Patent and Trademark Office*